United States Patent
Imai et al.

[11] Patent Number: 5,256,945
[45] Date of Patent: Oct. 26, 1993

[54] ORGANIC ELECTROLUMINESCENCE ELEMENT

[75] Inventors: Kunio Imai; Masanao Shinkai; Takeo Wakimoto, all of Saitama; Yasuhiko Shirota, Toyonaka, all of Japan

[73] Assignee: Pioneer Electronic Corporation, Tokyo, Japan

[21] Appl. No.: 806,287

[22] Filed: Dec. 13, 1991

[30] Foreign Application Priority Data

Apr. 8, 1991 [JP] Japan .................................. 3-075212

[51] Int. Cl.$^5$ .......................... H05B 33/14; H01J 1/62
[52] U.S. Cl. .................. 313/504; 252/301.16; 428/457
[58] Field of Search ................... 313/504; 252/301.16; 428/457

[56] References Cited
U.S. PATENT DOCUMENTS 4,720,432  1/1988  VanSlyke et al. ................. 313/498
5,104,740  4/1992  Shinkai et al. ...................... 313/504

Primary Examiner—Sandra L. O'Shea
Attorney, Agent, or Firm—Foley & Lardner

[57] ABSTRACT

An organic EL element comprises a cathode, an EL layer of organic compound, a first hole transport layer of organic compound, a second hole transport layer of organic compound and an anode which are laminated in sequence, wherein the second hole transport layer is made of a substance represented by the following chemical formula 1:

(Chemical formula 1)

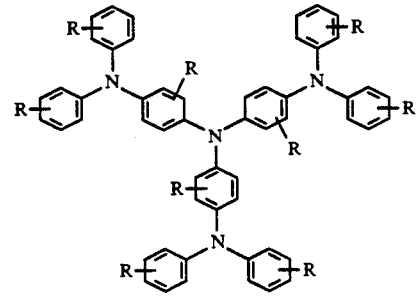

where R each independently represents a hydrogen atom, an alkyl group of from 1 to 6 carbon atoms, a halogen group, a cyano group, a nitro group, a primary, secondary or tertiary amino group, or an aryl group of from 6 to 15 carbon atoms. This organic EL element prevents a leakage current and emits light stably for a long time.

12 Claims, 2 Drawing Sheets

EMMISION

EMMISION

EMMISION

EMMISION

EMMISION

ORGANIC ELECTROLUMINESCENCE ELEMENT

BACKGROUND OF THE INVENTION

1. Field of the invention

The present invention relates to an electroluminescence (EL) element having an EL layer made of an emitting substance, which utilizes electroluminescence phenomenon that the emitting substance emits light by applying an electric current to the EL layer. More particularly, it is concerned with an organic electroluminescence element (organic EL element) in which the EL layer is made of an organic emitting substance.

2. Description of the prior art

As prior art organic EL elements, there have been known an element of two-layer structure having two layers of organic compounds as shown in FIG. 1, in which an organic fluorescent thin film 3 (hereinafter referred as "EL layer") and an organic hole transport layer 4 are laminated with each other and are arranged between a metal cathode 1 and a transparent anode 2. There have been also known an element of three-layer structure having three layers of organic compounds as shown in FIG. 2, in which an organic electron transport layer 5, an EL layer and an organic hole transport layer 4 are laminated in sequence and are sandwiched as a whole between a metal cathode 1 and a transparent anode 2. The hole transport layer 4 facilitates the infusion of the holes from the anode and blocks electrons. The electron transport layer 5 facilitates the infusion of electrons from the cathode.

In these organic EL elements, a glass substrate 6 is furnished outside the transparent anode 2. The recombination of electrons infused from the metal cathode 1 and the holes infused from the transparent anode 2 to the EL layer 3 generates excitons. The excitons emit light when they are deactivated through radiation. This light radiates toward outside through the transparent anode 2 and the glass substrate 6 (See Japanese Patent Patent Laid-opens Nos.59-194393 and 63-295695).

The conventional organic EL elements constructed as indicated above generally emit light even at a low voltage. However, when the EL element formed with a simple matrix structure of electrode strips is continuously driven by a DC voltage, a leakage current occurs in a cross portion of the electrode strips. As a result, the portion not to emit light, i.e. the periphery of the cross portion, may emit light, and/or such an EL element easily becomes destructible. Further, there are strong demands on an organic EL element emitting light at a high luminance in the industrial market.

SUMMARY OF THE INVENTION

An object of the present invention is to provide an organic EL element, which can prevent the leakage current and stably emit light for a long time and at a high luminance.

The organic EL element according to the present invention comprises a cathode, an EL layer of organic compound, a first hole transport layer of organic compound, a second hole transport layer of organic compound and an anode which are laminated in sequence, wherein the second hole transport layer is made of a substance represented by the following chemical formula 1:

(Chemical formula 1)

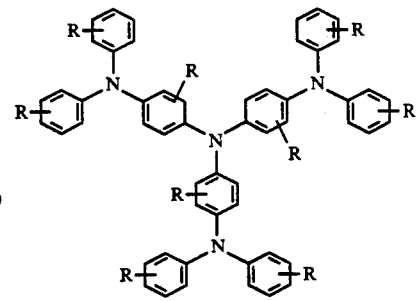

-continued where R each independently represents a hydrogen atom, an alkyl group of from 1 to 6 carbon atoms, a halogen group, a cyano group, a nitro group, a primary, secondary or tertiary amino group, or an aryl group of from 6 to 15 carbon atoms.

DETAILED DESCRIPTION OF PREFERRED EMBODIMENTS

The embodiments according to the present invention will be described in more detail with reference to the drawings.

Figure 1:
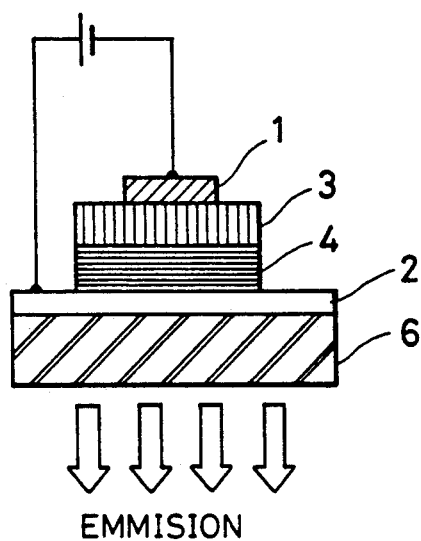
FIG. 1 is a schematic diagram showing an organic EL element with two-layer structure.
Figure 2:
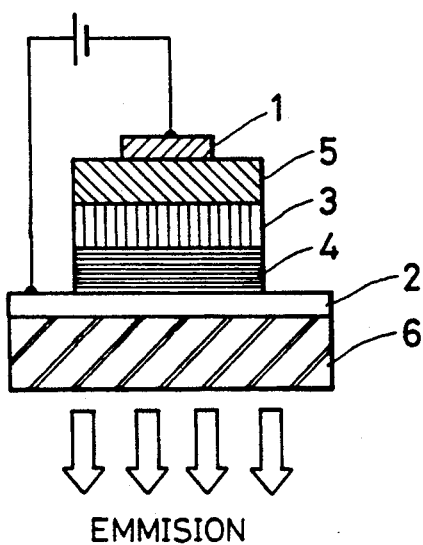
FIG. 2 is a schematic diagram showing an organic EL element with three-layer structure.
Figure 3:
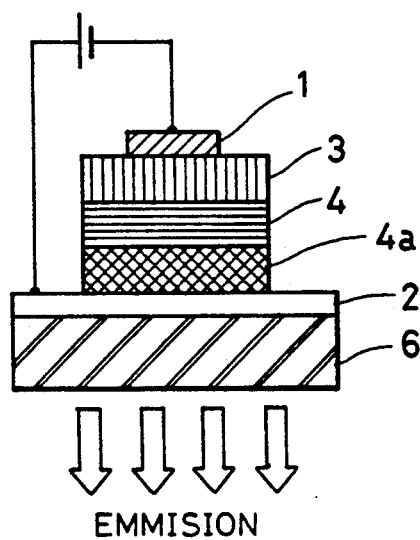
FIG. 3 is a schematic diagram showing an organic EL element with three-layer structure according to the present invention.
Figure 4:
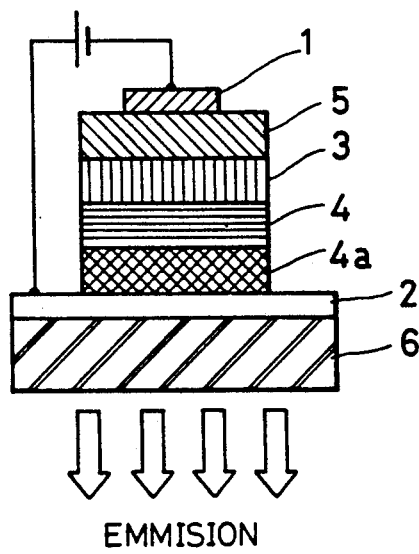
FIG. 4 is a schematic diagram showing an organic EL element with 4-layer structure according to the present invention.

As shown in FIG. 3, a first embodiment of organic EL element according to the present invention comprises an EL layer 3, a first hole transport layer 4 and a second hole transport layer 4a which are laminated and formed as thin films between a pair of metal cathode 1 and transparent anode 2. A second embodiment of organic EL element according to the present invention comprises an electron transport layer 4, an EL layer 3, a first hole transport layer 4 and a second hole transport layer 4a which are arranged between a pair of metal cathode 1 and a transparent anode 2 as shown in FIG. 4. In any of these cases, it will suffice if either the electrode 1 or 2 is transparent. The cathode 1 is formed of a metal with a lower work function such as aluminum, magnesium, indium, silver or alloy of these metals in the thickness range of from about 100 to 5000 Å. The transparent anode 2 is formed of an electroconductive material with a higher work function such as indium-tin oxide (ITO) in the thickness range of from about 1000 to 3000 Å. The transparent anode 2 may be formed of gold with the thickness of from about 800 to 1500 Å. The electrode of gold thin film is semitransparent.

The second hole transport layer 4a is made of the electroluminescent compound represented by the chemical formula 1 such as 4, 4', 4" -tris[N-(3-methylphenyl)-N-phenylamino] triphenylamine (hereinafter referred as "MTDATA") and 4, 4', 4" -tris(N,N-diphenylamino) triphenylamine ("TDATA") respectively denoted by the following formulas 2 and 3:

(Chemical formula 2)

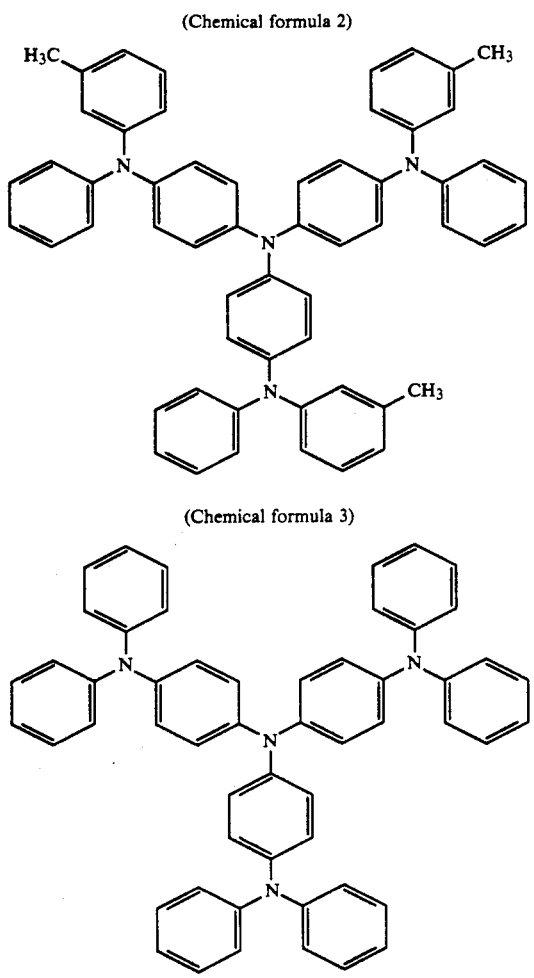

(Chemical formula 3)

Both MTDATA and TDATA have the melting points of about 203° C. or more and the glass transition points of about 75° C., each showing a high heat-resistant property. Also, each of MTDATA and TDATA has a twisted molecular structure and three dimensional frameworks. Thus, these triphenylamine derivatives are easily crystallized and have excellent shielding properties against another substance. Even when a thin film made of one of such triphenylamine derivatives is left at the temperature lower than room temperature for several months, it is not crystallized. Therefore the triphenylamine derivative film maintains its excellent thin film forming property. Further, MTDATA and TDATA have high electric conductivities in the order of $10^{-10}$ sec/cm. MTDATA and TDATA can be used as the materials desirable for forming EL layer 3.

Next, it is preferable that the first hole transport layer is made of N, N' -diphenyl-N-N'-bis(3-methylphenyl)-1,1'-biphenyl-4,4'-diamine (hereinafter referred as "TPD") represented by the following chemical formula 4. Further, the compounds known as CTM (carrier transporting materials) represented by the following chemical formulas 5 to 15 are suitably used alone or as mixture for the first hole transport layer.

(Chemical formula 4)

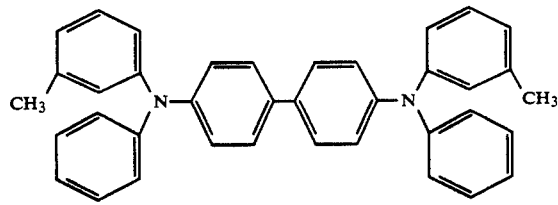

(Chemical formula 5)

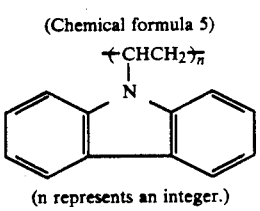

(n represents an integer.)

(Chemical formula 6)

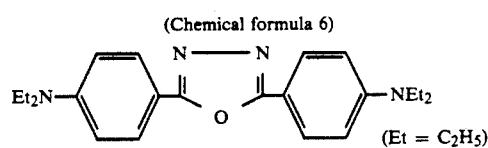

(Et = $C_2H_5$)

(Chemical formula 7)

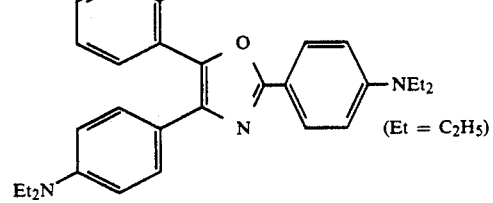

(Et = $C_2H_5$)

(Chemical formula 8)

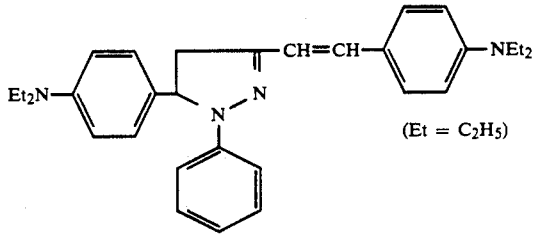

(Et = $C_2H_5$)

(Chemical formula 9)

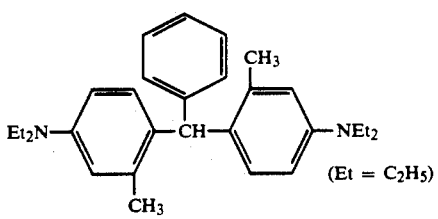

(Et = $C_2H_5$)

(Chemical formula 10)

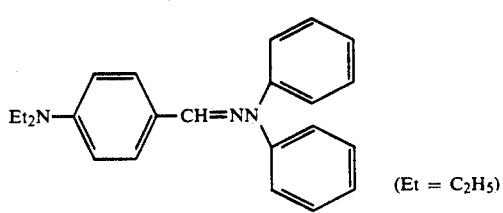

(Et = $C_2H_5$)

(Chemical formula 11)

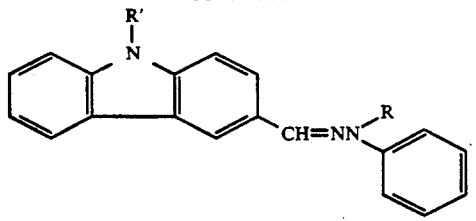

(R and R' represents an alkyl group).

(Chemical formula 12)

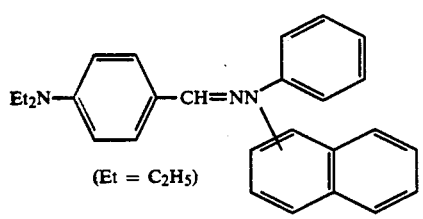

(Et = C₂H₅)

(Chemical formula 13)

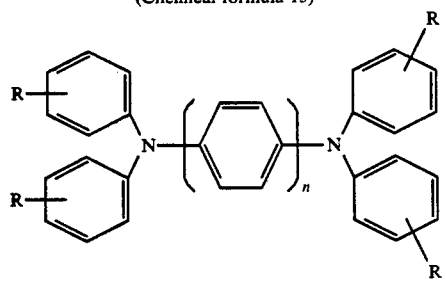

(R represents an alkyl group, and n is an integer.)

(Chemical formula 14)

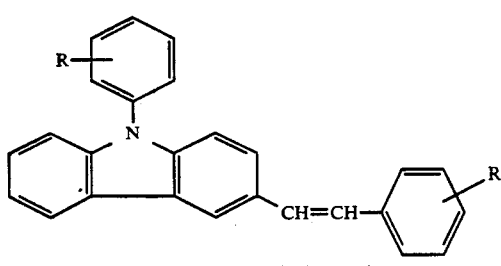

(R represents an alkyl group.)

(Chemical formula 15)

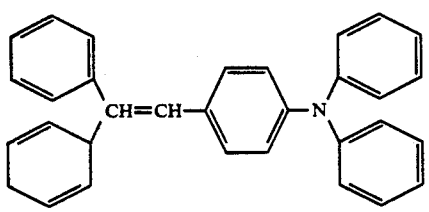

The EL layer 3 of the organic EL element comprises the organic fluorescent compound such as Aluminum oxine chelate (hereinafter referred as "Al$_{q3}$") and tetraphenylbutadiene (TPB) derivative respectively represented by the following chemical formulas 16 and 17, which may include another fluorescent compound as a guest material.

(Chemical formula 16)

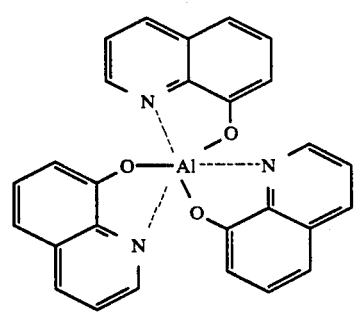

(Chemical formula 17)

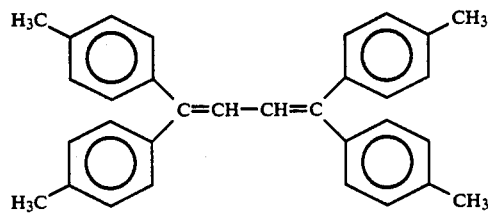

The electron transport layer 5 of organic EL element is preferably made of Bu-PBD [2-(4'-tert-butylphenyl)-5-(biphenyl)-1,3,4-oxadiazole] represented by the following chemical formula 18. Examples of suitable organic compounds which may be employed as the electron transport layer 5 are represented by the following chemical formulas 19 to 28.

(Chemical formula 18)

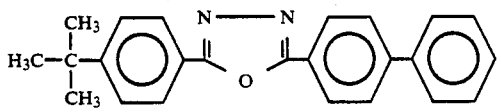

(Chemical formula 19)

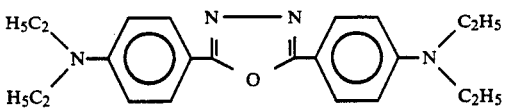

(Chemical formula 20)

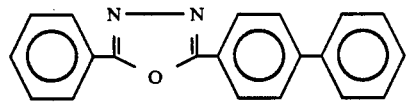

(Chemical formula 21)

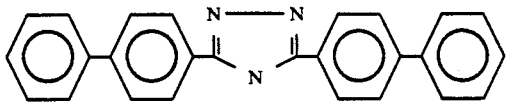

(Chemical formula 22)

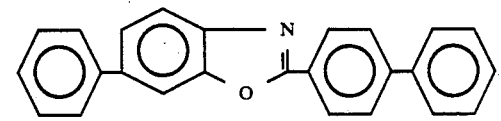

(Chemical formula 23)

-continued
(Chemical formula 24)

(Chemcial formula 25)

(Chemical formula 26)

(Chemical formula 27)

(Chemcial formula 28)

As described above, the organic EL element according to the present invention comprises the organic EL layer and the first organic hole transport layer laminated with each other and arranged between the cathode and the anode, is characterized in that the second hole transport layer made of triphenylamine derivatives represented by the chemical formula 1 is provided between the first hole transport layer and the anode. The second hole transport layer has the high heat property. Thus, the second hole transport layer reduces the undesirable influence thereon caused by the heat generated from application of electric current. The second hole transport layer has the excellent thin film forming property, it can therefore cover well and deposit even on an irregular surface of the anode. The second hole transport layer then prevents the sharp edge of the anode from coming closer to the cathode. Since the second hole transport layer has the high conductivity, the voltage applied thereon decreases and the heating is minimized. In this way, it is possible according to the present invention to improve the durability of the organic EL element which emits light at a high luminance and a high efficiency upon application of a low voltage.

EXAMPLE 1

A well washed glass substrate was prepared, on which an anode of ITO had been formed. MTDATA of chemical formula 2 was heated under vacuum conditions and deposited on the ITO anode with the thickness of 200 Å as the second hole transport layer. Next, TPD of chemical formula 4 was heated under vacuum conditions and deposited on the MTDATA layer with the thickness of 300 Å as the first hole transport layer. Then, $Al_{q3}$ of chemical formula 16 was heated under vacuum conditions and deposited on the TPD layer with the thickness of 500 Å as the EL layer. Next, magnesium and aluminum were vacuum deposited on the EL layer of $Al_{q3}$ with the thickness of 1500 Å under vacuum conditions at the vacuum deposition rate of 10 Å /sec and 1 Å /sec respectively as the metal alloy cathode. In this way, the EL element was manufactured.

When the resultant EL element was operated with the application of DC voltage at the constant current density of 10 mA/cm$^2$ for 600 hours, then its output luminance was attenuated from the initial 400 cd/m$^2$ to the elapsed 225 cd/m$^2$, while the increase of the applied voltage was only 2 V during this time period. This shows a high driving stability of the EL element.

COMPARATIVE EXAMPLE 1

As an EL element was produced by the same procedure as in the above Example 1, excepting that the second hole transport layer made of MTDATA was not formed.

When this EL element was operated at the constant current density of 10 mA/cm$^2$ for about 250 hours, a leakage current occurred at points other than the light-emitting points. This El element therefore did not emit light, showing an instability as an EL element.

EXAMPLE 2

Instead of EL layer of $Al_{q3}$ in the Example 1, an EL element was assembled by the same procedure as in the Example 1 while using EL layer of TPB derivative represented by chemical formula 17.

When this EL element was operated at the constant current density of 50 mA/cm$^2$ for about 175 hours, the initial output luminance of 80 cd/m$^2$ was attenuated to the elapsed output luminance of 10 cd/m$^2$, while the increase of the applied voltage was only 2 V during this time period. This shows a high driving stability of the EL element.

COMPARATIVE EXAMPLE 2

An EL element was assembled by the same procedure as in the Example 2, except that the second hole transport layer made of MTDATA of the Example 2 was not formed.

When this EL element was operated at the constant current density of 27 mA/cm$^2$ for about 10 hours, the luminance was attenuated from 80 cd/m$^2$ to 1 cd/m$^2$, and the element was destroyed.

COMPARATIVE EXAMPLE 3

An EL element was assembled by the same procedure as in the Example 2, except that Bu-PBD represented by the above chemical formula 18 was vacuum-deposited and laminated with the thickness of 300 Å as the electron transport layer.

When this EL element was continuously driven the hue of emitted light was changed within a short time and it was destroyed. When such an EL element was operated at the constant current density of 5 mA/cm$^2$, it emitted light at 80 cd/m$^2$, but it was destroyed in 3 hours while the hue was changed from blue to white.

COMPARATIVE EXAMPLE 4

Instead of the second hole transport layer made of MTDATA of the Example 2, an EL element was assembled by the same procedure as in the Example 2, except that the second hole transport layer made of Cu-Ph represented by the following chemical formula 29 was used.

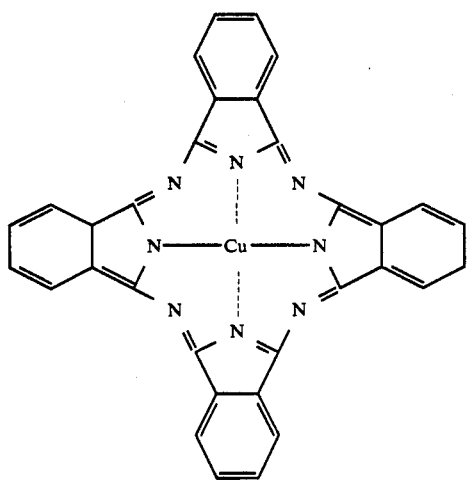

When this EL element was operated at the constant current density of 27 mA cm² for about 19 hours, its luminance was attenuated from 80 cd/m² to 0 cd/m².

What is claimed is:

1. An organic electroluminescence element, comprising a cathode, an EL layer of organic compound, a first hole transport layer of organic compound, a second hole transport layer of organic compound and an anode which are laminated in sequence, wherein the second hole transport layer is made of a substance represented by the following chemical formula 1:

(Chemical formula 1)

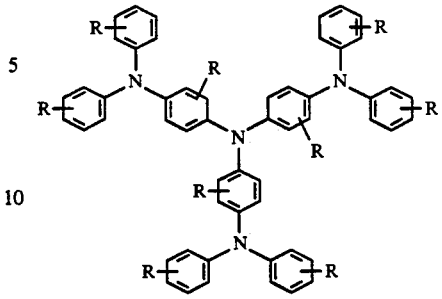

where R each independently represents a hydrogen atom, an alkyl group of from 1 to 6 carbon atoms, a halogen group, a cyano group, a nitro group, a primary, secondary or tertiary amino group, or an aryl group of from 6 to 15 carbon atoms.

2. An organic electroluminescence element according to claim 1, wherein an organic electron transport layer is provided between said cathode and said EL layer.

3. An organic electroluminescence element according to claim 1, wherein the second hole transport layer is made of 4,4'4''-tris[N-(3-methylphenyl)-N-phenylamino]triphenylamine.

4. An organic electroluminescence element according to claim 1, wherein the second hole transport layer is made of 4,4',4''-tris(N,N-diphenylamino)-triphenylamine.

5. An organic electroluminescence element according to claim 1, wherein the first hole transport layer is made of (N,N'-diphenyl)-N,N'-bis(3-methylphenyl)-1,1'-biphenyl-4,4'-diamine.

6. An organic electroluminescence element according to claim 5, wherein the electron transport layer is made of 2-(4'-tert-butylphenyl)-5-(biphenyl)-1,3,4-oxadiazole.

7. An organic electroluminescence element according to claim 1, wherein the EL layer is made of one of aluminum oxine chelate and tetraphenylbutadiene.

8. An organic electroluminescence element according to claim 2, wherein the second hole transport layer is made of 4,4',4''-tris[N-(3-methylphenyl)-N-phenylamino]triphenylamine.

9. An organic electroluminescence element according to claim 2, wherein the second hole transport layer is made of 4,4',4''-tris(N,N-diphenylamino)-triphenylamine.

10. An organic electroluminescence element according to claim 2, wherein the first hole transport layer is made of (N,N'-diphenyl)-N,N'-bis(3-methylphenyl)-1,1'-biphenyl-4,4'-diamine.

11. An organic electroluminescence element according to claim 10, wherein the electron transport layer is made of 2-(4'-tert-butylphenyl)-5-(biphenyl)-1,3,4-oxadiazole.

12. An organic electroluminescence element according to claim 2, wherein the EL layer is made of one of aluminum oxine chelate and tetraphenylbutadiene.

* * * * *